United States Patent [19]

Gross

[11] 4,076,928

[45] Feb. 28, 1978

[54] SUBSTANTIALLY DRY WATER SWELLABLE PARTICULATE POLYELECTROLYTE

[75] Inventor: James R. Gross, Lake Jackson, Tex.

[73] Assignee: The Dow Chemical Company, Midland, Mich.

[21] Appl. No.: 606,147

[22] Filed: Aug. 20, 1975

Related U.S. Application Data

[62] Division of Ser. No. 494,439, Aug. 5, 1974.

[51] Int. Cl.$^2$ .................. C08F 220/34; B29B 1/02
[52] U.S. Cl. .................. 526/240; 260/29.6 HN; 260/29.6 TA; 260/33.4 R; 260/79.3 M; 264/144; 264/216; 526/304; 526/317
[58] Field of Search .................. 264/216, 144; 260/79.3 M, 33.4 R, 29.6 TA, 29.6 HN; 128/156, 296, 284; 526/240, 304, 317

[56] References Cited

U.S. PATENT DOCUMENTS

| | | | |
|---|---|---|---|
| 2,701,391 | 2/1955 | Yost et al. | 264/216 |
| 3,808,305 | 4/1974 | Gregor | 264/216 |
| 3,957,710 | 5/1976 | Rohmann et al. | 260/29.6 TA |

FOREIGN PATENT DOCUMENTS 1,209,333  10/1970  United Kingdom.

*Primary Examiner*—James B. Lowe
*Attorney, Agent, or Firm*—Benjamin G. Colley

[57] ABSTRACT

Water swellable absorbent articles, made from copolymers having a copolymerized crosslinker, together with methods for their preparation, and a composition containing a copolymerized crosslinker useful to make said articles are disclosed. The copolymers comprise 25–98% by weight of an alkali metal salt of an olefinically unsaturated monosulfonic or monocarboxylic acid, about 2–50% by weight of an olefinically unsaturated monocarboxylic acid and about 0.1–5.0% by weight of an N-substituted acrylamide or methacrylamide. The articles are crosslinked by heating and/or removing substantially all of the water from the precursor composition.

The crosslinked compositions, in the form of a film, can be disintegrated to form flakes, strips or powders.

The absorbent articles are useful as surgical sponges, diapers, tampons, meat trays, bath mats and the like.

6 Claims, No Drawings

SUBSTANTIALLY DRY WATER SWELLABLE PARTICULATE POLYELECTROLYTE

CROSS-REFERENCE TO RELATED APPLICATION

This is a divisional, of application Ser. No. 494,439, Filed Aug. 5, 1974.

BACKGROUND OF THE INVENTION

This invention relates to water swellable absorbent articles made from crosslinked polyelectrolytes, methods for their preparation, and to a composition consisting of polyelectrolytes containing a copolymerized crosslinker which is useful to make absorbent articles.

It is known from U.S. Pat. Nos. 3,669,103 and 3,670,731 that cross-linked polymeric sorbents can be sandwiched between flexible supports to achieve disposable diapers or dressings.

It is further known from U.S. Pat. Nos. 2,988,539; 3,393,168; 3,514,419 and 3,557,067 that water swellable cross-linked carboxylic copolymers can be prepared. However, these prior art copolymers are all crosslinked during copolymerization or crosslinked after polymerization with subsequent neutralization of the carboxylic acid groups to form water swellable polyelectrolytes and hence these prior art polyelectrolytes cannot be crosslinked in situ as a coating on a substrate or as a flexible film thereof.

It is known from Ser. No. 468,794 filed April 9, 1974, now U.S. Pat. No. 3,980,663, and Ser. No. 450,650 filed March 13, 1974, now U.S. Pat. No. 3,926,891, that water swellable cured articles can be made from polyelectrolytes that have been crosslinked after polymerization with the addition of special crosslinking compounds prior to the heating or curing step.

The present invention is an improvement over these inventions in that the crosslinking agent is built into or copolymerized with polyelectrolytes during polymerization. The advantage of this invention is that only a single solution needs to be sent to users and the chance of operator error in the mixing of the crosslinking agents is eliminated.

SUMMARY OF THE INVENTION

The present invention comprises a composition which is useful to form water swellable articles of a carboxylic type synthetic polyelectrolyte which consists of a solvent such as lower alcohols, water, or mixtures thereof, about 5 to about 60 percent, preferably about 15 to about 40 percent by weight based on the solvent of a carboxylic copolymer which contains in the copolymer (A) about 25 to about 98% by weight based on the total weight of the copolymer of an alkali metal salt of an olefinically unsaturated monosulfonic or monocarboxylic acid, (B) about 2 to about 50% by weight of an olefinically unsaturated monocarboxylic acid, and (C) about 0.1 to about 5.0% by weight of an N-substituted acrylamide or methacrylamide wherein the substituent group is a hydroxymethylene or an alkoxymethylene group having 1–8 carbons in the alkyl group.

The invention further comprises methods of making discrete films, absorbent articles, particulates, fibers, and the products of these processes wherein the above composition on various substrates, is heated to a temperature greater than about 30° C. and preferably from about 90° to about 150° C. The use of these elevated temperatures is advantageous to accelerate the crosslinking and drying of the polyelectrolyte.

In order to obtain very high production rates of absorbent articles, it may be desirable to replace part or nearly all of the water in the polyelectrolyte solution with a lower alcohol such as methanol or ethanol. This substitution results in lower solution viscosities at a given percent solids and promotes rapid drying.

The final products of the present invention are thus water swellable and are useful whereever aqueous solutions need to be absorbed. Examples of the diverse utilities are surgical sponges, catamenial tampons, diapers, meat trays, paper towels, disposable door mats, disposable bath mats and disposable litter mats for household pets.

DETAILED DESCRIPTION OF THE INVENTION

The mechanism through which the polyelectrolytes of this invention cure themselves (i.e. without an added curing agent) involves the condensation of a pendant carboxylic acid group on one polymer chain with a substituted amide group on another polymer chain with the resulting elimination of a molecule of water or alcohol. This reaction is thermo dynamically possible at any temperature but for all practical purposes only proceeds at elevated temperatures. Since the reaction is dependent on two separate species coming together in solution, the rate is concentration dependent and once the composition is applied to a substrate and evaporation of solvent begins, the rate of cross-linking accelerates. Applying heat of this time increases the rate even more.

If the cross-linking rection is allowed to occur in the original solution as by heating or prolonged storage, the absorbent article of this invention cannot be fabricated. The solution will become progressively more viscous and stringy until it forms a continuous gel which cannot be spread, sprayed, or spun.

The process for making the crosslinkable solution of polyelectrolytes of this invention briefly consists of copolymerizing one mole of an olefinically unsaturated carboxylic acid, or a mixture thereof wherein an olefinically unsaturated sulfonic acid, replaces up to 95% of the carboxylic acid with 0.001 to 0.1 moles of an N-substituted acrylamide or methacrylamide in the presence of 0.4 to 0.95 moles of an alkali metal hydroxide and 0.0 to 0.05 moles of a free radical initiator. The temperature at which the reaction takes place can range from 5° to 100° C.

Examples of the useful olefinically unsaturated carboxylic acids used are acrylic, methacrylic, itaconic, monomethylmaleate, and the like.

Examples of the olefinically unsaturated sulfonic acids are styrene sulfonic acid, vinylbenzylsulfonic acid and vinylsulfonic acid.

Examples of the useful free radical initiators used are sodium persulfate, ammonium persulfate, potassium persulfate and the like.

The N-substituted acrylamides that are useful in this invention have the following generic formula:

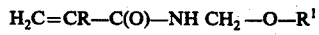

$$H_2C=CR-C(O)-NH\ CH_2-O-R^1$$

wherein R is selected from hydrogen or methyl and $R^1$ is hydrogen or an alkyl group of 1–8 carbons.

Examples of these N-hydroxymethyl or N-alkoxymethylene acrylamides or methacrylamides are N-methoxymethyl acrylamide, N-propoxymethyl acrylamide,
N-ethoxymethyl acrylamide,
N-isopropoxymethyl acrylamide,
N-methylol acrylamide,
N-butoxymethyl acrylamide,
N-tetiarybutoxymethyl acrylamide,
N-isobutoxymethyl acrylamide,
N-octyloxymethyl acrylamide,
N-methyoxymethyl methacrylamide,
N-propoxymethyl methacrylamide,
N-ethoxymethyl methacrylamide,
N-isopropoxymethyl methacrylamide,
N-methylol methacrylamide,
N-butoxymethyl methacrylamide,
N-tetiarybutoxymethyl methacrylamide,
N-isobutoxymethyl methacrylamide, and
N-octyloxymethyl methacrylamide.

In the method of making water swellable films by the present invention, the above composition of the polyelectrolytes is spread on a flat plate or roller of metal, plastic, or other impervious substrate and heated to a temperature greater than 30° C. to crosslink the polyelectrolyte and drive off the excess water and/or alcohol. The film is then peeled off the plate or roller by a scraper to recover the intact film for subsequent storage or use.

It is sometimes desirable to add a small amount of a surfactant to the polyelectrolyte composition to aid in flowing on and removing the continuous film from the water impervious substrate. A secondary benefit of using a surfactant is to increase the wettability of the final dry absorbent film. Either anionic or nonionic surfactants may be used. Examples of the useful surfactants are the sodium alkyl sulfonates and ethylene oxide derivatives of alkylated phenols and the like.

Similarly, when an absorbent article is prepared, the article which is to be the substrate is coated with the acidified composition of the polyelectrolyte and then the coating is crosslinked. It is to be understood that for the purposes of this invention the coating step implies a complete coating or a discontinuous coating, thus when a fibrous substrate such as cellulose batting, paper, woven or nonwoven cloth, and the like are used as the substrate, the composition can be applied in a discontinuous manner, i.e. in a pattern of large dots, squares, or grid lines to retain the inherent flexibility of the fiberous substrate and at the same time vastly improve its water absorbency. In this instance plasticizers are not needed. Wood pulp can be coated by slurrying it in the polyelectrolyte composition followed by a fluffing operation.

If desired, the water swellable film prepared as above can be used per se as the inner absorbent layer in baby diapers. It is sometimes advantageous that the film be disintegrated into flakes, strips or powders. This is accomplished by crushing or comminuting the film in a hammer mill, blenders, or the like. If long flat strips are desired, the fim can be sliced widthwise with appropriate slicers.

In some instances, water swellable fibers are desired. These can be prepared by extruding the above composition of the polyelectrolytes into a bath comprising lower alkyl ketones such as acetone, methyl ethyl ketone, diethyl ketone and the like. Alcoholic compositions may be extruded into a non-aqueous coagulent such as chlorinated hydrocarbons, i.e. methylene chloride, perchloroethylene and the like. The soft extruded fibers are then removed from the bath by any convenient means such as a three or five roll cluster and carried through a heated chamber at a temperature greater than about 30° C and preferably in the range from about 70° to about 150° C. to dry and to crosslink the polyelectrolyte fibers.

The absorbency of the crosslinked polyelectrolytes (grams solution gelled per gram of polyelectrolyte) is determined in the following manner using synthetic urine (0.27 N sodium chloride solution).

A 0.5 gram sample of a crosslinked polyelectrolyte is weighed into a 250 ml. beaker, a 0.27 N sodium chloride solution (150 ml.) is poured into the beaker and allowed to soak for 2 hours at room temperature, with occasional stirring. The swelled polyelectrolyte is then collected by filtration and the gel capacity is reported as grams of solution gelled per gram of polymer salt.

The following examples are presented solely to illustrate but not limit the invention.

EXAMPLE 1

Acrylic acid (19.48 g), deionized water (61 g), 50% sodium hydroxide (19.15 g), N-methylolacrylamide (0.41 g of 60% solution), and sodium persulfate (0.5 g) are charged to a screw-cap 4 oz. bottle. The bottle is sealed, shaken, and placed in a 50° water bath for 16 hours. The extremely viscous solution was then diluted with an equal volume of water and spread on a mirror finish chrome plate with a 30 mil draw bar. After air drying to a clear film, the film was further dried in a 150° oven for 2 hours. One gram of this cured film absorbed 49 g of 0.27 N NaCl solution to give a firm, readily filtered gel.

EXAMPLE 2

Acrylic acid (5.0 g), sodium styrene sulfonate (19.87 g), deionized water (75 g), and N-methylolacrylamide (0.21 g of 60% solution) were charged to a 4 oz. screw-cap bottle and treated as in Example 1. The dried and cured film of this heteropolymer absorbed 31 g of salt solution per gram of film.

Following the procedure of Example 2 9.95 grams of sodium styrene sulfonate, 0.05 grams of N-methyol acrylamide, 30 grams of water and 0.5 (5% by weight) grams of acetic acid were reacted for 16.5 hours at 50° C.

A film was cast from the resulting solution and cured at 150° C for 5 hours. The film was found to be completely water soluble and not water swellable. This is believed to illustrate the fact that a copolymerized acid is needed to achieve a crosslinked and water swellable product.

EXAMPLE 3

According to the procedure of Example 2, acrylic acid (5.0 g), sodium styrene sulfonate (19.94 g), deionized water (75 g), and N-methylolacrylamide (0.1 g of 60% solution) were used. The film was dried and cured. The film absorbed 60 g salt solution per gram of film.

EXAMPLE 4

Example 1 was repeated except that N-isobutoxymethylacrylamide (0.41 g of 60% solution) was used in place of N-methylolacrylamide. Films prepared from the resulting solution absorbed 31 g of salt solution per gram of film.

I claim:

1. A substantially dry water swellable particulate polyelectrolyte produced by the method which comprises 1. preparing a solution,
   I. which comprises a solvent selected from the group consisting of water, lower alcohols and mixtures thereof, and
   II. about 5 to about 60% by weight based on (I) of a crosslinkable carboxylic copolymer which contains in the copolymer
      A. about 25 to about 98% by weight based on the total weight of the copolymer of units derived from an alkali metal salt of an olefinically unsaturated monosulfonic or monocarboxylic acid;
      B. about 2 to about 50% by weight of units derived from an olefinically unsaturated monocarboxylic acid; and
      C. about 0.1 to about 5.0% by weight of units derived from an N-substituted acrylamide or methacrylamide having the formula $$H_2C=CR-C(O)-NHCH_2-O-R'$$

wherein R is selected from hydrogen or methyl and R' is hydrogen or an alkyl group of 1–8 carbons,
2. spreading a coating of said solution on an impervious substrate,
3. heating said coated substrate to a temperature greater than about 30° C to crosslink said polyelectrolyte,
4. separating said crosslinked polyelectrolyte film from said substrate, and
5. disintegrating said film to form flakes, strips, or powders thereof.

2. The particulate polyelectrolyte as set forth in claim 1 wherein the crosslinkable carboxylic copolymer contains 90 weight percent of units derived from sodium acrylate, 9 weight percent of units derived from acrylic acid and 1.0 weight percent of units derived from N-methylolacrylamide.

3. The particulate polyelectrolyte as set forth in claim 1 wherein the crosslinkable carboxylic copolymer contains 79 weight percent of units derived from sodium styrene sulfonate, 20 weight percent of units derived from acrylic acid and 1.0 weight percent of units derived from N-methylolacrylamide.

4. The particulate polyelectrolyte as set forth in claim 1 wherein the crosslinkable carboxylic copolymer contains 90 weight percent of units derived from sodium acrylate, 9 weight percent of units derived from acrylic acid and 1.0 weight percent of units derived from N-isobutoxymethylacrylamide.

5. The particulate polyelectrolyte as set forth in claim 1 wherein the crosslinkable carboxylic copolymer contains 79.7 weight percent of units derived from sodium acrylate, 20 weight percent of units derived from acrylic acid, and 0.3 weight percent of units derived from N-methylolacrylamide.

6. The particulate polyelectrolyte as set forth in claim 1 wherein the crosslinking agent is N-isobutoxymethyl acrylamide.